US010598622B2

(12) United States Patent
Suzumura et al.

(10) Patent No.: US 10,598,622 B2
(45) Date of Patent: Mar. 24, 2020

(54) PERMEABILITY EVALUATION METHOD

(71) Applicant: HITACHI CHEMICAL COMPANY, LTD., Tokyo (JP)

(72) Inventors: Koji Suzumura, Tokyo (JP); Kazuhiro Yamamoto, Tokyo (JP); Tomoko Murahashi, Tokyo (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 327 days.

(21) Appl. No.: 15/304,430

(22) PCT Filed: Apr. 15, 2014

(86) PCT No.: PCT/JP2014/060726
§ 371 (c)(1),
(2) Date: Oct. 14, 2016

(87) PCT Pub. No.: WO2015/159367
PCT Pub. Date: Oct. 22, 2015

(65) Prior Publication Data
US 2017/0038324 A1 Feb. 9, 2017

(51) Int. Cl.
*G01N 27/06* (2006.01)
*G01N 15/08* (2006.01)
(Continued)

(52) U.S. Cl.
CPC .......... *G01N 27/06* (2013.01); *C09J 133/068* (2013.01); *G01N 13/00* (2013.01); *G01N 15/08* (2013.01); *G01N 2013/003* (2013.01)

(58) Field of Classification Search
CPC ........ G01N 27/06; G01N 27/26; G01N 13/00; G01N 15/08; G01N 2013/003; C09J 133/068
See application file for complete search history.

(56) References Cited

U.S. PATENT DOCUMENTS

| | | | |
|---|---|---|---|
| 2006/0157355 A1* | 7/2006 | Baskaran | C25D 3/02 205/674 |
| 2009/0308762 A1 | 12/2009 | Tiedtke | |
| 2011/0001500 A1* | 1/2011 | Uchiyama | G01N 27/302 324/705 |

FOREIGN PATENT DOCUMENTS

| | | |
|---|---|---|
| CN | 201163274 A | 12/2008 |
| CN | 203164096 A | 8/2013 |
| | (Continued) | |

OTHER PUBLICATIONS

EPO computer-generated English language translation of JP-07130809-A downloaded Mar. 13, 2019 (Year: 2019).*

(Continued)

*Primary Examiner* — Maris R Kessel
(74) *Attorney, Agent, or Firm* — Fitch, Even, Tabin & Flannery, LLP

(57) ABSTRACT

A permeability evaluation method for evaluating permeability of heavy metal ions through a specimen, comprising a step of, in a state in which a first liquid containing heavy metal ions and a second liquid containing water and an organic solvent are separated by a specimen, applying a voltage between a positive electrode provided on the side of the first liquid and a negative electrode provided on the side of the second liquid and measuring the value of the current flowing between the positive electrode and the negative electrode, wherein the specimen contains an insulating material used in semiconductor production, and the heavy metal ion concentration of the first liquid is 0.5 mg/kg or more.

28 Claims, 5 Drawing Sheets

(51) Int. Cl.
*G01N 13/00* (2006.01)
*C09J 133/06* (2006.01)

(56) References Cited

FOREIGN PATENT DOCUMENTS

| DE | 102005040592 A1 | * | 3/2007 | ............ G01N 27/49 |
|----|----|----|----|----|
| JP | S61-226637 A | | 10/1986 | |
| JP | H3-248039 A | | 11/1991 | |
| JP | H05-326661 A | | 12/1993 | |
| JP | 07130809 A | * | 5/1995 | |
| JP | 2000-040726 A | | 2/2000 | |
| JP | 2000040726 A | * | 2/2000 | |
| JP | 2002156359 A | * | 5/2002 | |
| JP | 2009-541754 A | | 11/2009 | |
| JP | 2011-213878 A | | 10/2011 | |
| JP | 2011-222779 A | | 11/2011 | |
| JP | 2012-216621 A | | 11/2012 | |
| JP | 2012-216622 A | | 11/2012 | |
| JP | 2012216622 A | * | 11/2012 | |
| JP | 2012-241157 A | | 12/2012 | |
| WO | 2008/000400 A2 | | 1/2008 | |

OTHER PUBLICATIONS

EPO computer-generated English language translation of JP-2000040726-A downloaded Mar. 13, 2019 (Year: 2019).*
EPO computer-generated English language translation of JP-2002156359-A downloaded Mar. 13, 2019 (Year: 2019).*
EPO computer-generated English language translation of JP-2012216622-A downloaded Mar. 13, 2019 (Year: 2019).*
EPO computer-generated English language translation of DE-102005040592-A1 downloaded Mar. 13, 2019 (Year: 2019).*
International Preliminary Report on Patentability (IPRP) of WO Appln. No. PCT/JP2014/060726 dated Oct. 27, 2016.
Notice of Allowance of JP Patent Application No. P2016-513530 dated Dec. 5, 2017.
International Search Report of WO Appln. No. PCT/JP2014/060726 dated Jun. 3, 2014 in English.

\* cited by examiner (a)

(b)

(c)

(a)

(b)

(c)

PERMEABILITY EVALUATION METHOD

TECHNICAL FIELD

The present invention relates to a permeability evaluation method for heavy metal ions. Specifically, the present invention relates to a permeability evaluation method that can easily and quickly evaluate the permeability of heavy metal ions through a specimen containing an insulating material used in semiconductor production.

BACKGROUND ART

In recent years, in accordance with high performance and high speed operation of smartphones, tablet PCs and the like, for semiconductor packages used therefor, further downsizing, high capacity, high speed operation and thinning have been required. Thus, in wafers used in semiconductor packages, further miniaturization of interconnects proceeds, and additionally, chips tend to become further thinner on assembling packages.

In such trends, particularly in the field of DRAM and NAND type flash memories in recent years, the problem of the occurrence of malfunctions due to a trace amount of heavy metal ions such as copper ions has become obvious.

It has been long known that when heavy metal ions come in contact with a silicon crystal, the ions diffuse in the crystal and reach the circuit surface, and as a result, a malfunction occurs. Therefore, it is common to conduct gettering treatment on a silicon wafer for capturing heavy metal ions such that the heavy metal ions attached to the silicon wafer do not diffuse to the circuit surface.

As the gettering treatment, for example, a method of providing a gettering layer within the wafer (intrinsic gettering, referred to as "IG" hereinbelow) and a method of providing a gettering layer on the back side of a wafer (extrinsic gettering, referred to as "EG" hereinbelow) are predominantly used. However, thickness of the gettering layer that can be formed inside is becoming thinner because of thinning of chips in recent years, and it is becoming hard to say that its effect is sufficient. Additionally, in EG, fine cracks are formed on the back side of a wafer, and therefore, flexural strength of the chip decreases. Thus, particularly in ultrathin wafers of which handling is difficult, the problem of excessive gettering treatment being difficult to conduct has occurred. Under such circumstances, imparting a gettering function to a die bonding film used for adhesion between a chip and a substrate or between a chip and a chip has been contemplated in recent years (for example, see Patent Literatures 1 and 2 below).

However, in the case of determining if a gettering function is imparted by such materials, it is necessary to make an evaluation after a package is actually prepared using a substrate on which a wiring layer is formed or a wafer on which a circuit is formed. In this case, there is a problem that a large amount of cost, a long period of time, apparatuses and the like may become required.

Under such situations, a new evaluation method has been contemplated for determining if a material for semiconductors has a gettering ability or not. For example, in the Patent Literature 3 below, there is represented a method in which one side of a silicon wafer is contaminated with heavy metal, the heavy metal is allowed to diffuse by heating, a film, which is an object to be evaluated, is applied to the contaminated one side, and after thermal treatment under pseudo reflow conditions, the amount of heavy metal ions on the other side of the silicon wafer (no contaminated side) is measured, Furthermore, in the Patent Literature 4 below, there is represented a method in which a film, which is an object to be evaluated, is applied to one side of a silicon wafer, the film surface is contaminated with heavy metal, and then, thermal treatment is conducted under pseudo reflow conditions, and the amount of heavy metal ions on the other side of the silicon wafer (the side to which no film is applied) is measured.

CITATION LIST

Patent Literature

Patent Literature 1: Japanese Unexamined Patent Publication No. 2011-213878
Patent Literature 2: Japanese Unexamined Patent Publication No. 2012-241157
Patent Literature 3: Japanese Unexamined Patent Publication No. 2012-216621
Patent Literature 4: Japanese Unexamined Patent Publication No. 2012-216622

SUMMARY OF INVENTION

Technical Problem

It is considered that either method is excellent as a method to directly confirm an ability of an object to be evaluated to preferentially getter heavy metal or an ability of an object to be evaluated to suppress passage of heavy metal. However, either method uses a fluoric acid, which is extremely hazardous, on quantifying the heavy metal in a silicon wafer, and also requires an environment of high cleanliness. Furthermore, because tasks leading to the evaluation are complex, the methods are effective as a temporary evaluation method but are not suitable as a steady evaluation method for product test on product shipping and the like, for example.

Additionally, in the above Patent Literature 2, evaluation is made based on the amount of heavy metal ions adsorbed on a film which becomes an object to be evaluated. However, in this case, the evaluation is easy as an evaluation method, but is not suitable, for example, as an evaluation method for permeability of heavy metal ions in a contaminated substrate, additionally, influences of a migration phenomenon of a heavy metal complex produced by complex formation in a film, for example, are not taken into account.

The present invention has been made in the view of such a problem, and it is an object of the present invention to provide a permeability evaluation method that can easily and quickly evaluate the permeability of heavy metal ions through a specimen containing an insulating material used in semiconductor production.

Solution to Problem

The present inventors, as a result of intensive studies, have found that the above problem may be solved by a specific evaluation method of, in a state in which a first liquid containing heavy metal ions and a second liquid containing water and an organic solvent are separated by a specimen, applying a voltage between a positive electrode provided on the side of the first liquid and a negative electrode provided on the side of the second liquid, as a permeability evaluation method of evaluating the permeability of heavy metal ions through a specimen containing an insulating material used in semiconductor production.

A permeability evaluation method of a first embodiment of the present invention is a permeability evaluation method for evaluating the permeability of heavy metal ions through a specimen, wherein the method comprises a step of, in a state in which a first liquid containing heavy metal ions and a second liquid containing water and an organic solvent are separated by a specimen, applying a voltage between a positive electrode provided on the side of the first liquid and a negative electrode provided on the side of the second liquid and measuring the value of the current flowing between the positive electrode and the negative electrode, the specimen contains an insulating material used in semiconductor production, and the copper ion concentration of the first liquid is 0.5 mg/kg (=ppm) or more.

A permeability evaluation method of a second embodiment of the present invention is a permeability evaluation method for evaluating the permeability of heavy metal ions through a specimen, wherein the method comprises a step of, in a state in which a first liquid containing heavy metal ions and a second liquid containing water and an organic solvent are separated by a specimen, after a voltage is applied between a positive electrode provided on the side of the first liquid and a negative electrode provided on the side of the second liquid, measuring the heavy metal ion concentration of the second liquid, the specimen contains an insulating material used in semiconductor production, and the copper ion concentration of the first liquid is 0.5 mg/kg (=ppm) or more.

According to the permeability evaluation method of the present invention, it is possible to easily and quickly evaluate the permeability of heavy metal ions through a specimen containing an insulating material used in semiconductor production. According to the permeability evaluation method of the present invention, it is possible to easily evaluate the permeability of heavy metal ions in a short period without using a special apparatus. Additionally, the permeability evaluation method of the present invention is applicable to steady evaluations for product test and the like. Furthermore, according to the permeability evaluation method of the present invention, the getterability of heavy metal ions and permeability of heavy metal ions can be simultaneously evaluated.

The second liquid preferably contains N-methyl-2-pyrrolidone as the organic solvent. The content of N-methyl-2-pyrrolidone of the second liquid is preferably 20% by mass or more and 60% by mass or less.

The electrical conductivity of the second liquid is preferably 1 μS or more at 23° C.

The first liquid may contain copper ions as the heavy metal ions. The copper ion concentration of the first liquid is preferably 50000 mg/kg or less.

The insulating material used in the semiconductor production may be adhesive tape for semiconductors.

Advantageous Effects of Invention

According to the present invention, it is possible to provide a permeability evaluation method that can easily and quickly evaluate the permeability of heavy metal ions through a specimen containing an insulating material used in semiconductor production. According to the permeability evaluation method of the present invention, it is possible to easily evaluate the permeability of heavy metal ions in a short period without using a special apparatus. Additionally, the permeability evaluation method of the present invention is applicable to steady evaluations for product test and the like. Furthermore, according to the permeability evaluation method of the present invention, the getterability of heavy metal ions and permeability of heavy metal ions can be simultaneously evaluated.

DESCRIPTION OF EMBODIMENTS

Figure 1:
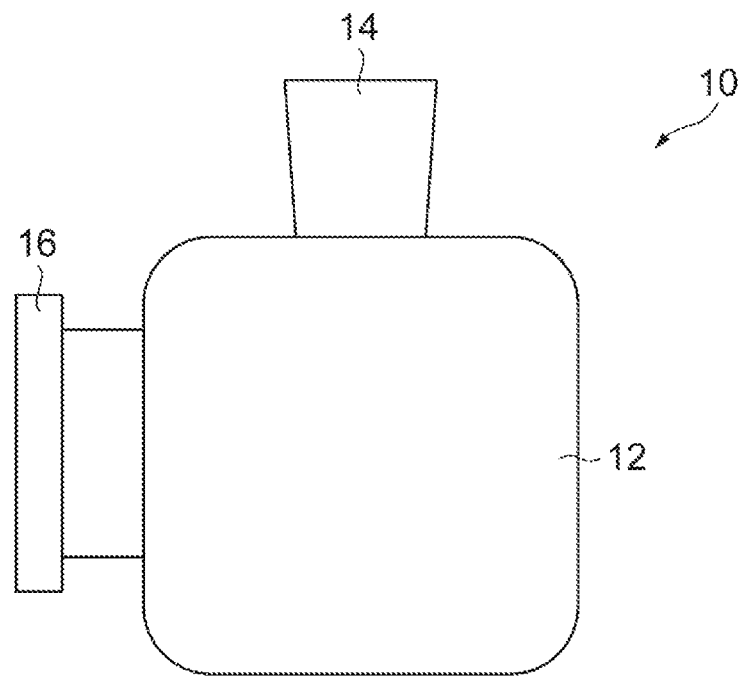
FIG. 1 is a schematic view showing one example of a cell used for evaluation of the permeability of heavy metal ions.

Hereinafter, embodiments to implement the present invention will be described in detail with referring to the drawings as required. However, the present invention is not limited to the following embodiments.

The permeability evaluation method of the present embodiment (in some cases, simply referred to as the "evaluation method" hereinbelow) is a permeability evaluation method that evaluates the permeability of heavy metal ions through a specimen containing an insulating material used in semiconductor production (insulating material for semiconductors). The evaluation method of the present embodiment, in a state in which liquid A (first liquid) and liquid B (second liquid) are separated by a specimen, applies a voltage between a positive electrode provided on the side of the liquid A and a negative electrode provided on the side of the liquid B. The liquid A contains heavy metal ions. The liquid B contains water and an organic solvent. The heavy metal ion concentration of the liquid A is 0.5 mg/kg or more. The evaluation method of the present embodiment comprises (I) a step of, in a state in which liquid A and liquid B are separated by a specimen, applying a voltage between a positive electrode provided on the side of the liquid A and a negative electrode provided on the side of the liquid B and measuring the value of the current flowing between the positive electrode and the negative electrode, or (II) a step of, in a state in which liquid A and liquid B are separated by a specimen, after applying a voltage between a positive electrode provided on the side of the liquid A and a negative electrode provided on the side of the liquid B, measuring the heavy metal ion concentration of the liquid B. In the step (I), the permeability of the heavy metal ions through the specimen is evaluated based on the value of the current flowing between the positive electrode and the negative electrode. In the step (II), the permeability of the heavy metal ions through the specimen is evaluated based on the heavy metal ion concentration of the liquid B.

The specimen is not particularly limited as long as it contains an insulating material and has an insulation property. Examples of the shape of the specimen include films and sheets. Insulating materials which are liquid at ordinary temperature (23° C.) can be used as long as the insulating materials are materials cured and solidified by heat, light beams, electron beams or the like. Examples of the insulating material used in semiconductor production include adhesive films and adhesive pastes used for adhesion between a chip and a chip or between a chip and a substrate; Non- Conductive Films and Non-Conductive Pastes used for flip chip connection; underfill materials; solder resists used in materials for protecting substrate surface; and buffer coating materials used for protecting chip circuit surface. Among these, in the case where adhesive tape for semiconductors (adhesive films for semiconductors) such as adhesive films used for adhesion between a chip and a chip or between a chip and a substrate, it is possible to evaluate the permeability more suitably. The insulating material used in semiconductor production contains at least one selected from, for example, resins (epoxy resin, phenol resin, vinyl resin, acrylic resin, phenoxy resin, polyamide resin, polyimide resin, polyamide-imide resin, silicone resin and the like), inorganic fillers (silica filler, alumina filler, titanium oxide filler, carbon filler and the like), silane coupling materials, curing accelerators, acrylic monomers, methacrylic monomers, and vinyl compounds.

In the evaluation method of the present embodiment, for example, two cells separated via a specimen are employed. The material, size and the like of the cells are not limited. Examples of the material of the cells include various glasses, various metals, and various resins. Among these, cells for which various glasses or various resins are employed are preferred because there is no influence of metal impurities contained in the material itself. Glass is preferred because it is stiffer than resins and thus, the cell is difficult to deform, and because it is transparent and thus, the state of the electrodes and the state of each liquid are easy to observe during measurement. Here, the volume (the amount of liquid that can be contained) of a cell (for example, a transmission cell such as a glass cell) is not particularly limited, but 10 ml or more and 1000 ml or less is preferred considering the ease of producing the cell and the labor of waste fluid after measurement.

The measuring apparatus comprises two cells separated via a specimen, which is an object to be measured. The shape of each cell is not particularly limited as long as the shape is such that the liquid A with which one cell is filled and the object to be measured are in direct contact with each other as well as the liquid B with which the other cell is filled and the object to be measured are in direct contact with each other and such that the liquid A and the liquid B are not intermixed with each other. The cell containing the liquid A and the cell containing the liquid B may be the same or different.

FIG. 1 is a schematic view showing one example of a cell used for evaluation of the permeability of heavy metal ions. As shown in FIG. 1, a cell 10 has a cell body 12, an opening portion (sampling opening, electrode inlet) 14, and a flange portion (specimen contact portion, specimen mounting portion) 16. The cell body 12 has an interior space that can hold liquid. The opening portion 14 is tubular and placed on the top of the cell body 12. The interior space of the cell body 12 communicates with the outside via the opening portion 14. The flange portion 16 is tubular (for example, toric) and placed at the side of the cell body 12. The interior space of cell body 12 communicates with the outside via the flange portion 16.

Figure 2:
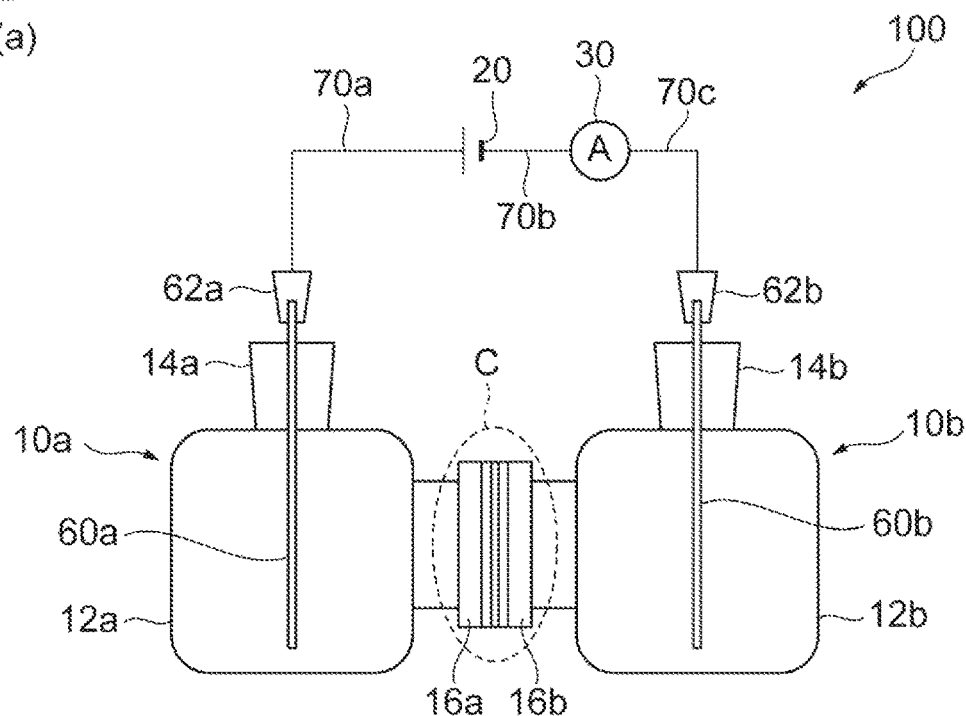
FIG. 2 is a schematic view showing one example of a measuring apparatus used for evaluation of the permeability of heavy metal ions.
Figure 2:
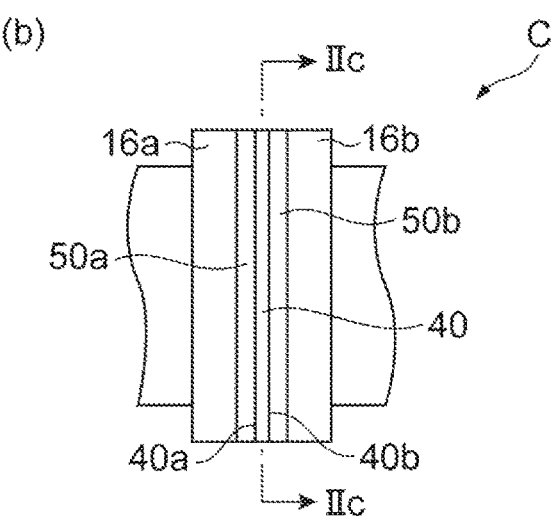
Figure 2:
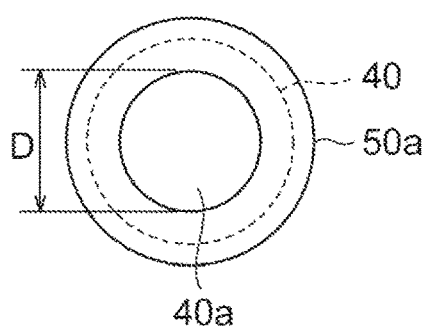

FIG. 2 is a schematic view showing a measuring apparatus used for evaluation of the permeability based on a current value, as one example of a measuring apparatus used for evaluation of the permeability of heavy metal ions. FIG. 2 (a) is a view showing the entire measuring apparatus. FIG. 2 (b) is an enlarged view showing the connecting portion C of the cells. FIG. 2 (c) is a schematic sectional view along the line IIc-IIc of FIG. 2 (b). The measuring apparatus 100 comprises a first cell 10a, a second cell 10b, a direct-current power supply 20 and an ammeter 30, as shown in FIG. 2 (a).

The cells 10a and 10b, which have a similar structure as the cell 10 in FIG. 1, are transmission cells, for example. The cell 10a has a cell body 12a, an opening portion 14a and a flange portion 16a. The cell 10b has a cell body 12b, an opening portion 14b and a flange portion 16b. In the interior space of the cell body 12a, liquid A is contained. In the interior space of the cell body 12b, liquid B is contained.

As shown in FIG. 2 (b), the flange portion 16a of the cell 10a and the flange portion 16b of the cell 10b are connected to each other via a first packing 50a, a specimen 40 and a second packing 50b. For example, the specimen 40, which is circular, has a first main surface 40a, and a second main surface 40b opposite to the main surface 40a.

The packing 50a is annular (for example, toric) and in contact with the flange portion 16a. The packing 50b is annular (for example, toric) and in contact with the flange portion 16b. The specimen 40 is placed between the packing 50a and the packing 50b. The main surface 40a of the specimen 40 is in contact with the packing 50a. The main surface 40b of the specimen 40 is in contact with the packing 50b.

As shown in FIG. 2 (c), the flange portions 16a and 16b, the specimen 40, the packings 50a and 50b are arranged such that the central axes of these members are aligned. For example, in the case where the capacity of each cell is 50 ml, the diameter of the cell bottom is 4.5 cm and the height of the cell is 4.5 cm, the inner diameter D of the packings 50a and 50b is from 0.5 to 2.0 cm. The inner diameter of the flange portions 16a and 16b is, for example, from 0.5 to 2.5 cm. The outer diameter of the packings 50a and 50b is for example, from the inner diameter D+0.2 cm to the inner diameter D+1.0 cm. The diameter of the specimen 40 is, for example, from the inner diameter D+0.2 cm to the inner diameter D+2.0 cm. The thickness of the specimen 40 is, for example, from 0.0005 to 0.02 cm (from 5 to 200 µm).

The liquid A contained in the cell 10a is in contact with the main surface 40a of the specimen 40 at the flange portion 16a. The liquid B contained in the cell 10b is in contact with the main surface 40b of the specimen 40 at the flange portion 16b. The liquid A and the liquid B are separated via the specimen 40.

Into the interior space of the cell 10a, a positive electrode 60a is inserted through the opening portion 14a. The lower end side (one end side) of the positive electrode 60a is in contact with the liquid A by being immersed in the liquid A in the interior space of the cell 10a. The upper end side (the other end side) of the positive electrode 60a is located outside the opening portion 14a. A clip 62a is attached to the upper end of the positive electrode 60a. The clip 62a has electrical conductivity.

Into the interior space of the cell 10b, a negative electrode 60b is inserted through the opening portion 14b. The lower end side (one end side) of the negative electrode 60b is in contact with the liquid B by being immersed in the liquid B in the interior space of the cell 10b. The upper end side (the other end side) of the negative electrode 60b is located outside the opening portion 14b. A clip 62b is attached to the upper end of the negative electrode 60b. The clip 62b has electrical conductivity.

The positive electrode side of the direct-current power supply 20 is connected to the clip 62a via electric wiring 70a. The negative electrode side of the direct-current power supply 20 is connected to the ammeter 30 via electric wiring 70b. The direct-current power supply 20 and the ammeter 30 are serially connected. The ammeter 30 is connected to the clip 62b via electric wiring 70c.

Figure 3:
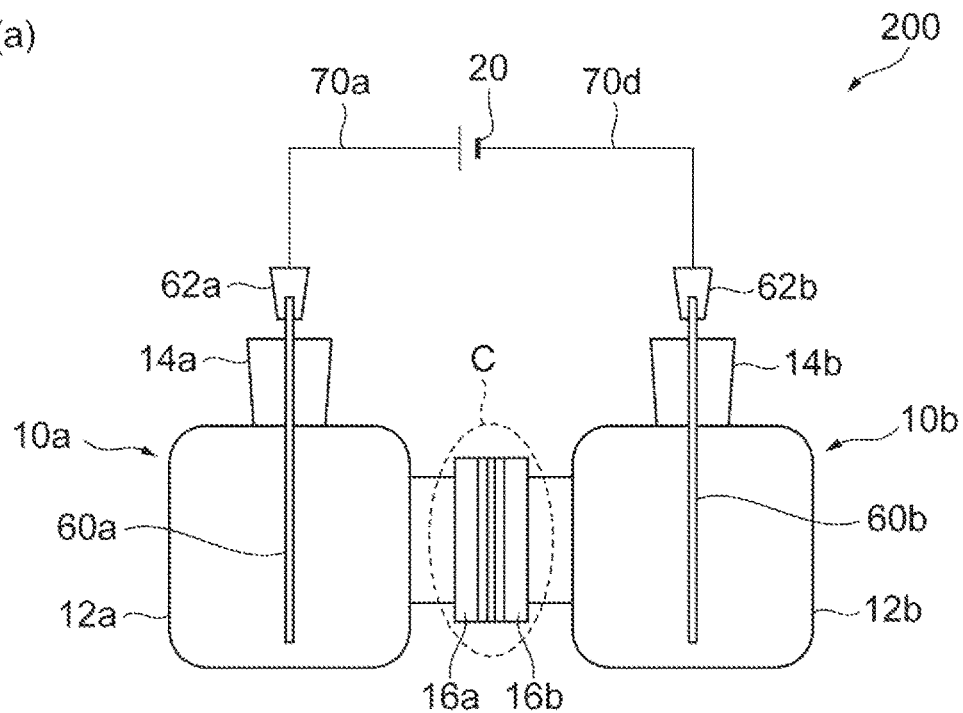
FIG. 3 is a schematic view showing one example of a measuring apparatus used for evaluation of the permeability of heavy metal ions.
Figure 3:
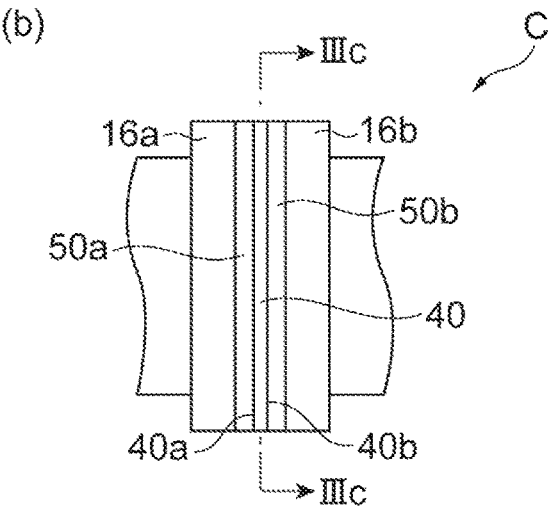
Figure 3:
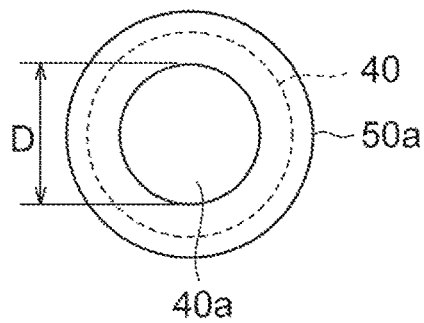

FIG. 3 is a schematic view showing a measuring apparatus used for evaluation of the permeability based on a heavy metal ion concentration, as one example of a measuring apparatus used for evaluation of the permeability of heavy metal ions. FIG. 3 (a) is a view showing the entire measuring apparatus. FIG. 3 (b) is an enlarged view showing the connecting portion C of the cells. It is a schematic sectional view along the line IIIc-IIIc of FIG. 3 (b). A measuring apparatus 200 has a similar structure of the measuring apparatus 100 except that the measuring apparatus 200 does not comprise the ammeter 30 and that the direct-current power supply 20 and the clip 62b are in direct contact with each other via electric wiring 70d.

The liquid A is preferably a solution obtained by mixing a heavy metal salt comprising heavy metal ions (ionic compound) and a solvent and dissolving the heavy metal salt in the solvent. When the liquid A containing the heavy metal ions (cations) is contained in the cell on the positive electrode side, the heavy metal ions contained in the liquid A pass through the specimen, which is an object to be measured, to thereby migrate to the cell on the negative electrode side by applying a voltage between the positive electrode and the negative electrode. Thereby, it is possible to measure the permeability of the heavy metal ions through the specimen.

Examples of the heavy metal ions contained in the liquid A include, but are not particularly limited to, iron ions, lead ions, gold ions, platinum ions, silver ions, copper ions, chromium ions, cadmium ions, mercury ions, zinc ions, arsenic ions, manganese ions, cobalt ions, nickel ions, molybdenum ions, tungsten ions, tin ions, and bismuth ions. Among these, particularly, copper ions are preferred from the viewpoint of higher permeability of an insulating material used in semiconductor production. Examples of the heavy metal salt include chloride salts, sulfate salts, acetate salts, iodide salts, and nitrate salts. The heavy metal salt is more preferably easy to dissolve in a solvent (for example, water) (for example, the solubility in water of 23° C. is 0.5 mg/kg or more). Examples of such a soluble copper metal salt include copper(I) chloride, copper(II) chloride, copper (I) sulfate, copper(II) sulfate, copper(I) acetate, copper(II) acetate, copper(I) iodide, and copper(II) nitrate.

The liquid A is preferably an aqueous solution. Being an aqueous solution makes it possible to use various heavy metal salts as well as makes it possible to adjust the aqueous solution to various concentrations. As the solvent for the liquid A, it is possible to use water, a protonic polar solvent, a non-protonic polar solvent, or a mixture of these as long as the specimen to be used for measurement is not dissolved in the solvent.

The heavy metal ion concentration (for example, copper ion concentration) of the liquid A is 0.5 mg/kg or more. Thereby, a sufficient amount of the heavy metal ions (for example, copper ions) is present, and thus, it is possible to evaluate the permeability of the heavy metal ions through the specimen. The heavy metal ion concentration (for example, copper ion concentration) of the liquid A is preferably the following concentration, from the viewpoint of passage of the heavy metal ions (for example, copper ions) through the specimen being easily detected by change in the current value and quantitative analysis of the heavy metal ions. The heavy metal ion concentration is preferably 5 mg/kg or more, from the viewpoint of the permeability of the heavy metal ions being easy to evaluate because a sufficient amount of the heavy metal ions (for example, copper ions) is present. The heavy metal ion concentration is preferably 50000 mg/kg or less, and more preferably 5000 mg/kg or less, from the viewpoint that precipitation of a part of the heavy metal during measurement is suppressed and from the viewpoint that excess increase in the amount permeated is suppressed and the significant difference of the permeability is easy to determine. The heavy metal ion concentration of the liquid A is the concentration before a voltage is applied between the positive electrode and the negative electrode, for example. In the case where a heavy metal salt (for example, copper metal salt) is used, the heavy metal ion concentration (for example, copper ion concentration) is preferably adjusted within the above range in terms of the heavy metal (for example, in terms of element copper).

The liquid B preferably do not contain heavy metal ions (for example, heavy metal salt). An organic solvent contained in the liquid B is preferably an organic solvent which is excellent in miscibility with water (for example, is completely mixed with water). It is possible to measure the permeability of the heavy metal ions further quickly by using a mixed solution of water and an organic solvent which is excellent in miscibility with water (for example, is completely mixed with water). Examples of the organic solvent excellent in miscibility with water include methanol, ethanol, 1-propanol, 2-propanol, tetrahydrofuran, N,N-dimethylformamide, and N-methyl-2-pyrrolidone. Among these, N-methyl-2-pyrrolidone is preferred from the viewpoint that the boiling point is high and the flammability of a mixed solution is low. As the liquid B, it is possible to use water, a protonic polar solvent, a non-protonic polar solvent, or a mixture of these as long as the specimen to be used for measurement is not dissolved in the solvent.

The content (mixing proportion) of the organic solvent (for example, N-methyl-2-pyrrolidone) is preferably 20% by mass or more, and more preferably 40% by mass or more, based on the total amount of the liquid B, from the viewpoint of the time required for the heavy metal ions to pass being shortened. The content of the organic solvent (for example, N-methyl-2-pyrrolidone) is preferably 80% by mass or less, and more preferably 60% by mass or less, based on the total amount of the liquid B, from the viewpoint that an extremely rapid permeation rate is suppressed and the significant difference of the permeability is easy to determine and from the viewpoint that dissolution of the specimen is easy to suppress.

The electrical conductivity of the liquid B is preferably 1 µS or more, and more preferably 200 µS or more at 23° C. When the liquid B has a slight electrical conductivity as described above, the time required for passage of the heavy metal ions is shortened, and thus it is possible to make an evaluation further quickly. The upper limit of the electrical conductivity of the liquid B is not particularly limited. It is possible to measure the electrical conductivity of the liquid B by using, for example, an SD Data Logger Multi Water Quality Meter CD-4307SD manufactured by MOTHER-TOOL CO., LTD.

An example of a method to adjust the electrical conductivity of the liquid B to 1 µS or more include addition of a small amount of a compound which is ionized in water. Examples of such a compound include light metal salts, inorganic salts (for example, sodium sulfate), acids and alkalis. Among these, light metal salts and inorganic salts (for example, sodium sulfate) are preferred from the viewpoint of the occurrence of the chemical change in the specimen being easy to suppress.

Electrodes (positive electrode and negative electrode) to be inserted into each cell will be described. The materials for the electrodes can be electrical conductors, and it is possible to use various materials, not limited to materials commercially available as electrodes. Furthermore, the electrodes may not be commercially available electrodes, as the electrodes, for example, a metal plate processed into an optional shape may be used, and leads of pencils, mechanical pencils and the like may be used without any change. Examples of the electrode include metal electrodes such as platinum, gold and palladium; and carbon electrodes (electrodes of carbon material). Among these, carbon electrodes are preferred from the viewpoint of being inexpensive.

Subsequently, the direct-current power supply will be described. As a direct-current power supply used for voltage application, there is no particular limitation, and it is possible to use a commercially available device. A voltage which can be output in the direct-current power supply is preferably 1 V or more, from the viewpoint that the time required for passage of the heavy metal ions is shortened and it is possible to make an evaluation further quickly.

The voltage to be applied between the positive electrode and the negative electrode on measurement differs depending on types of the specimen, the heavy metal ions, the liquid A and the liquid B, for example, in the case where a specimen (for example, adhesive tape for semiconductors) having the thickness of 20 μm is used, a copper sulfate aqueous solution is used as the liquid A, and a solution of water:N-methyl-2-pyrrolidone:sodium sulfate having the mass ratio of 50:50:0.05 is used as the liquid B, it is possible to make a measurement further quickly by applying about 6 to 24 V on the electrodes.

In the evaluation method of the present embodiment, a voltage is applied between the positive electrode and the negative electrode, and a permeation phenomenon of the heavy metal ions through the specimen is detected to thereby evaluate the permeability of the heavy metal ions through the specimen. As the method for detecting a permeation phenomenon of the heavy metal ions through the specimen, for example, it is possible to use a method in which, after a voltage is applied between the positive electrode and the negative electrode, the value of the current flowing between the positive electrode and the negative electrode is measured; and a method in which, after a voltage is applied between the positive electrode and the negative electrode, the heavy metal ion concentration of the liquid B is quantified.

In the method in which the value of the current flowing between the positive electrode and the negative electrode is measured, a voltage is applied between the positive electrode and the negative electrode, and the heavy metal ions transfers from the liquid A to the liquid B by permeating the specimen, and therefore, a slight current begins to flow between the liquid A and the liquid B separated by the specimen to thereby gradually increase the current value. The difference in the permeability can be evaluated by confirming the change in the current value (for example, the time required to reach the predetermined current value, the current value after the predetermined time). For example, it is possible to evaluate the permeability by obtaining both the time required to reach the predetermined current value in the case where the specimen which is an object to be measured is used and the time required to reach the predetermined current value in the case where specimen which is an object to be compared is used and by comparing the times required to each other. For example, it is possible to determine that the permeability is higher when the time required to reach the predetermined current value is shorter.

In the case of using the method for measuring the current value, the type of the ammeter used is not particularly limited, but, for example, it is possible to reproducibly evaluate the permeability of the heavy metal ions by using an ammeter of which the lower detection limit is 1 μA or more.

In the method for quantifying the heavy metal ion concentration of the liquid B, a voltage is applied between the positive electrode and the negative electrode, and therefore, the heavy metal ions transfers from the liquid A to the liquid B by permeating the specimen to thereby gradually increase the heavy metal ion concentration of the liquid B. The difference in the permeability can be evaluated by confirming the change in the heavy metal ion concentration (for example, the time required to reach the predetermined heavy metal ion concentration and the heavy metal ion concentration after the predetermined time). For example, it is possible to evaluate the permeability by obtaining both the time required to reach the predetermined heavy metal ion concentration in the case where the specimen which is an object to be measured is used and the time required to reach the predetermined heavy metal ion concentration in the case where specimen which is an object to be compared is used and by comparing the times required to each other. For example, it is possible to determine that the permeability is higher when the time required to reach the predetermined heavy metal ion concentration is shorter.

As the method for quantifying the heavy metal ion concentration of the liquid B, which is not particularly limited, for example, colorimetric analysis using the ion chromatograph method or the bathocuproine method or the like are used as a simple method.

The permeability evaluation method of the present embodiment may be used in a method for producing a semiconductor. For example, the method for producing a semiconductor of the present embodiment comprises a step of producing a semiconductor by using an insulating material used in semiconductor production, and a step of evaluating the permeability of the heavy metal ions through the specimen containing an insulating material used in semiconductor production by the permeability evaluation method of the present embodiment.

EXAMPLES

Hereinbelow, the present invention will be described more specifically with reference to Examples, but the present invention is not limited to these Examples. Chemicals used were all reagents, unless otherwise described.

[Preparation of Adhesion Film A for Die Adhesion]

After adding cyclohexanone to a composition consisting of 55 parts by mass of YDCN-703 (manufactured by Tohto Kasei Co., Ltd., product name, cresol novolak type epoxy resin, epoxy equivalent weight 210, molecular weight 1200, softening point 80° C.) as an epoxy resin, 45 parts by mass of MILEX XLC-LL (manufactured by Mitsui Chemicals, Inc., product name, phenol resin, hydroxyl group equivalent weight 175, water absorption coefficient 1.8%, heating mass reduction ratio at 350° C. 4%) as a phenol resin, 1.7 parts by mass of NUCA-189 (manufactured by Nippon Unicar Company Limited, product name, γ-mercaptopropyl trimethoxysilane) 3.2 parts by mass of NUCA-1160 (manufactured by Nippon Unicar Company Limited, product name, γ-ureidopropyl triethoxysilane) as silane coupling agents, and 32 parts by mass of AEROSIL R972 (a filler having organic groups such as methyl groups on the surface, which is obtained by covering silica surface with dimethyldichlorosilane followed by hydrolysis in a reactor at 400° C.; manufactured by NIPPON AEROSIL CO., LTD., product name, silica, average particle size 0.016 µm) as a filler, stirring and mixing were conducted, and then, kneading was conducted using a beads mill for 90 minutes.

Subsequently, after adding 280 parts by mass of acrylic rubber HTR-860P-3 containing 3% by mass of glycidyl methacrylate (manufactured by Nagase ChemteX Corporation, product name, weight average molecular weight 800000) and 0.5 parts by mass of curing accelerator CUREZOL 2PZ-CN (manufactured by Shikoku Chemicals Corporation, product name, 1-cyanoethyl-2-phenylimidazole), stirring and mixing were conducted. Additionally, vacuum degassing was conducted to thereby provide varnish.

After the varnish was applied onto a mold-releasing treated polyethylene terephthalate film having the thickness of 35 µm, heat-drying was conducted at 140° C. for five minutes to thereby form a coating film having the film thickness of 20 µm in a B-stage state, thereby, a die bonding film comprising a carrier film (adhesion film A for die adhesion, referred to as "adhesion film A" hereinafter) was prepared.

[Preparation of Adhesion Film B for Die Adhesion]

After adding 15 parts by mass of YDCN-703 (manufactured by Tohto Kasei Co., Ltd., product name, cresol novolak type epoxy resin, epoxy equivalent weight 210, molecular weight 1200, softening point 80° C.) as an epoxy resin, 12 parts by mass of MILEX XLC-LL (manufactured by Mitsui Chemicals, Inc., product name, phenol resin, hydroxyl group equivalent weight 175, water absorption coefficient 1.8%, heating mass reduction ratio at 350° C. 4%) as a phenol resin, and 200 parts by mass of spherical silica (manufactured by Admatechs Company Limited, product name: SO-25R, average particle size 0.5 µm) as a filler, and cyclohexanone, stirring and mixing were conducted, and then, kneading was conducted using a beads mill for 90 minutes.

Subsequently, after adding 200 parts by mass of acrylic rubber HTR-860P-3 containing 3% by mass of glycidyl methacrylate (manufactured by Nagase ChemteX Corporation, product name, weight average molecular weight 800000) and 0.2 parts by mass of curing accelerator CUREZOL 2PZ-CN (manufactured by Shikoku Chemicals Corporation, product name, 1-cyanoethyl-2-phenylimidazole), stirring and mixing were conducted. Additionally, vacuum degassing was conducted to thereby provide varnish.

After the varnish was applied onto a mold-releasing treated polyethylene terephthalate film having the thickness of 35 µm, heat-drying was conducted at 140° C. for five minutes to thereby form a coating film having the film thickness of 20 µm in a B-stage state, thereby, a die bonding film comprising a carrier film (adhesion film B for die adhesion, referred to as "adhesion film B" hereinafter) was prepared.

[Evaluation of Copper Contamination on Silicone Surface in Die with Adhesion Film]

A polyacrylic acid aqueous solution (Nv=25%, viscosity 8000 to 12000 mPa·s), a copper sulfate aqueous solution (500 mg/kg in terms of element copper) and distilled water were mixed as appropriate to thereby prepare a copper ion containing polyacrylic acid aqueous solution having Nv=1% and copper ion content of 5000 mg/kg (based on the solid content). This aqueous solution was cast onto a cover glass. Then, drying was conducted on a hot plate at 100° C. for 10 minutes followed by drying at 175° C. for 10 minutes to thereby prepare a glass substrate contaminated with copper ions.

A silicon wafer, having the thickness of 30 µm, of which the back surface was dry polished was diced into a size of 10 mm×10 mm to prepare silicone dies. Subsequently, the adhesion films A and B prepared above were cut into 10 mm×10 mm together with the carrier film. Then, the carrier film was peeled off, and the adhesion films A and B were each laminated onto the back surface side of the silicone dies at 80° C. to obtain silicone dies.

Subsequently, the silicone die onto which the adhesion film was laminated was die-attached onto the glass substrate contaminated with copper ions at 150° C. and 40 N for five seconds to prepare a sample 1.

The silicone die sample with a glass substrate-adhesion film (sample 1) was cured at 150° C. for an hour, then, at 175° C. for three hours, and furthermore, at 265° C. for an hour as the simple reflow conditions, to thereby prepare a sample 2.

After curing was completed, a cotton swab impregnated with N-methyl-2-pyrrolidone was used to lightly wipe the silicon wafer surface. Subsequently, a cotton swab impregnated with acetone was used to further conduct cleaning, and then, air drying was conducted at room temperature.

The silicone side surface of sample 1 and sample 2 were measured at five points by using time-of-flight secondary ion mass spectrometry (primary ion: Au, a neutralizing gun was used in combination, measurement region: 400 µm square). From the intensity of the copper ions in the positive ion mass spectrum and the intensity of the silicone portion on the substrate surface, the intensity ratio of the copper present on the silicone surface (Cu/Si intensity ratio, the average of five points) was determined. Additionally, as the rate of change in the intensity ratio, the rate of change of the intensity ratio of the sample 2 with respect to the intensity ratio of the sample 1 (intensity ratio of sample 2/intensity ratio of sample 1, rate of change in Cu/Si intensity) was determined. The results are shown in Table 1 below.

TABLE 1

| Adhesion film for die adhesion | Adhesion film A | | Adhesion film B | |
|---|---|---|---|---|
| Process | Sample 1 (Immediately after die attach) | Sample 2 (After simple reflow) | Sample 1 (Immediately after die attach) | Sample 2 (After simple reflow) |
| Cu/Si intensity ratio | 1.25E−04 | 9.54E−04 | 3.07E−04 | 1.12E−02 |
| Rate of change in Cu/Si intensity | 7.6 | | 36.5 | |

From the results, it can be seen that the adhesion film B tends to permeate the copper ions present on the substrate surface than the adhesion film A. Subsequently, based on these results, the permeability of heavy metal ions through the specimen was evaluated.

<Experiment A: Evaluation Based on Current Value>

Example 1

[Preparation of Liquid A]

A copper sulfate aqueous solution was prepared such that its copper ion concentration was adjusted to reach a concentration of 500 mg/kg in terms of element Cu by dissolving 2.0 g of anhydrous copper(II) sulfate in 1020 g of distilled water and sufficiently stirring until the copper sulfate was completely dissolved. This aqueous solution was used as liquid A.

[Preparation of Liquid B]

1.0 g of anhydrous sodium sulfate was dissolved to 1000 g of distilled water and stirring was sufficiently conducted until the sodium sulfate was completely dissolved. To this, 1000 g of N-methyl-2-pyrrolidone (NMP) was added and agitation was sufficiently conducted. Thereafter, air cooling was conducted so as to reach room temperature to thereby obtain a solution. This solution was used as liquid B.

The electrical conductivity of the liquid B (23° C.) was measured using an SD Data Logger Multi Water Quality Meter CD-4307SD manufactured by MOTHERTOOL CO., LTD. and it was 210 µS.

[Permeation Experiment] From the adhesion film A (thickness 20 µm) prepared above, a circle having the diameter of about 3 cm was cut out. Subsequently, two silicone packing sheets having the thickness of 1.5 mm, the outer diameter of about 3 cm and the inner diameter of 1.8 cm were prepared. The adhesion film A was sandwiched with the two silicone packing sheets. The adhesion film A sandwiched with the silicone packing sheets was sandwiched with the flange portions of two glass cells (cells having the structure in FIG. 1) having the capacity of 50 ml and fixed with a rubber band.

Subsequently, after 50 g of the liquid A was injected into one of the glass cells, 50 g of the liquid B was injected into the other glass cell. Mars Carbon manufactured by STAEDTLER (ϕ2 mm/130 mm) as a carbon electrode was inserted into each cell. The liquid A side was used as the positive electrode, and the liquid B side was used as the negative electrode, and the positive electrode was connected with a direct-current power supply (manufactured by A&D Company, Limited, a direct-current power supply apparatus AD-9723D). Additionally, the negative electrode and the direct-current power supply were connected in series via an ammeter (manufactured by SANWA ELECTRIC INSTRUMENT CO., LTD., Degital multimeter PC-720M). A voltage was applied at an applied voltage of 24.0 V, and measurement of the current value was started after application. This state was left at room temperature for 48 hours (2880 minutes).

After 48 hours (2880 minutes), the variation in the current value recorded in the ammeter was read, and the point at which the current value reached 10 µA was determined as the permeation time of the copper ions.

The permeation time of the copper ions through the adhesion film B (thickness 20 µm) was determined by a similar operation. Additionally, the permeation time ratio of the permeation time of the adhesion film A with respect to the permeation time of the adhesion film B (the permeation time of the adhesion film A/the permeation time of the adhesion film B) was calculated. The results are shown in Table 2 below.

Figure 4:
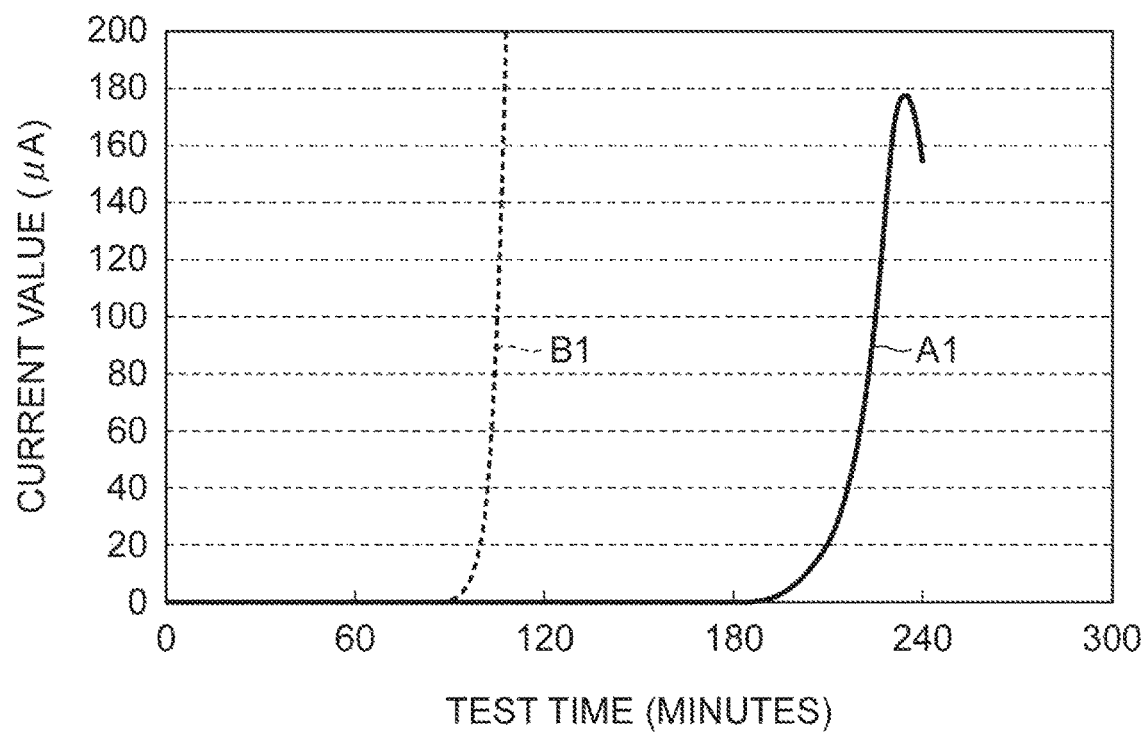
FIG. 4 is a view showing the measurement results of the current value of Example 1.

Also, the measurement results of the current value of Example 1 are shown in FIG. 4. In FIG. 4, the solid line A1 is the measurement result of the adhesion film A and the dotted line B1 is the measurement result of the adhesion film B.

Examples 2 to 4 and Comparative Examples 1 and 3

The evaluation was made in the same manner as in Example 1 except that the components of the liquid B were replaced by the components shown in Tables 2 and 3 below. The results are shown in Tables 2 and 3.

Comparative Example 2

The evaluation was made in the same manner as in Example 1 except that no voltage was applied. The results are shown in Table 3 below.

TABLE 2

|  |  | Unit | Example 1 | Example 2 | Example 3 | Example 4 |
|---|---|---|---|---|---|---|
| Liquid A | Solvent | — | Water | Water | Water | Water |
|  | Heavy metal species | — | Copper | Copper | Copper | Copper |
|  | Heavy metal concentration | mg/kg | 500 | 500 | 500 | 500 |
| Liquid B | Organic solvent species | — | NMP | NMP | NMP | NMP |
|  | Water/organic solvent proportion | Mass ratio | 50/50 | 50/50 | 40/60 | 20/80 |
|  | Additive species | — | Sodium sulfate | None | Sodium sulfate | Sodium sulfate |
|  | Electrical conductivity | µS | 210 | 8 | 210 | 210 |
|  | Voltage applied | V | 24.0 | 24.0 | 24.0 | 24.0 |
| Results | Adhesion film A | Minutes | 202 | 450 | 142 | 960 |
|  | Adhesion film B | Minutes | 89 | 190 | 56 | 390 |
|  | Permeation time ratio of adhesion film A/B | — | 2.3 | 2.4 | 2.5 | 2.5 |
|  | Remark | — | — | — | — | — |

TABLE 3

|  |  | Unit | Comparative Example 1 | Comparative Example 2 | Comparative Example 3 |
|---|---|---|---|---|---|
| Liquid A | Solvent | — | Water | Water | Water |
|  | Heavy metal species | — | Copper | Copper | Copper |
|  | Heavy metal concentration | mg/kg | 500 | 500 | 500 |

TABLE 3-continued

|  |  | Unit | Comparative Example 1 | Comparative Example 2 | Comparative Example 3 |
|---|---|---|---|---|---|
| Liquid B | Organic solvent species | — | None | NMP | NMP |
|  | Water/organic solvent proportion | Mass ratio | 100/0 | 50/50 | 0/100 |
|  | Additive species | — | None | Sodium sulfate | Sodium sulfate |
|  | Electrical conductivity | μS | 0.1 | 210 | 210 |
|  | Voltage applied | V | 24.0 | 0.0 | 24.0 |
| Results | Adhesion film A | Minutes | >2880 | >2880 | 3 |
|  | Adhesion film B | Minutes | >2880 | >2880 | 2 |
|  | Permeation time ratio of adhesion film A/B | — | — | — | 1.5 |
|  | Remark | — | No increase in current value | No increase in current value | Film dissolved partly |

As shown in the results of Examples, it is possible to easily and quickly evaluate the permeability of the heavy metal ions by using the permeability evaluation method of Examples, without requiring evaluation after the package was prepared. Meanwhile, in Comparative Example 1 where an organic solvent was not used in the liquid B, and Comparative Example 2 where no voltage was applied, it was not possible to quickly evaluate the permeability. Moreover, in Comparative Example 3 where water was not used, it was not possible to conduct measurement because the film, which would be an object to be measured, was dissolved.

<Experiment B: Evaluation Based on Heavy Metal Ion Concentration>

Example 5

The liquid A and the liquid B were prepared as in Example 1.

From the adhesion film A (thickness 20 μm) prepared above, a circle having the diameter of about 3 cm was cut out. Subsequently, two silicone packing sheets having the thickness of 1.5 mm, the outer diameter of about 3 cm and the inner diameter of 1.8 cm were prepared. The adhesion film A was sandwiched with the two silicone packing sheets. The adhesion film A sandwiched with the silicone packing sheets was sandwiched with the flange portions of two glass cells (cells having the structure in FIG. 1) having the capacity of 50 ml and fixed with a rubber band.

Subsequently, after 50 g of the liquid A was injected into one of the glass cells, 50 g of the liquid B was injected into the other glass cell. Mars Carbon manufactured by STAEDTLER (φ2 mm/130 mm) as a carbon electrode was inserted into each cell. The liquid A side was used as the positive electrode, and the liquid B side was used as the negative electrode, and the positive electrode and the negative electrode were connected via a direct-current power supply (manufactured by A&D Company, Limited, a direct-current power supply apparatus AD-9723D). A voltage was applied at an applied voltage of 24.0 V, and the copper ion concentration was measured by sampling the liquid B after application at regular intervals until 48 hours (2880 minutes).

The liquid B sampled was allowed to develop a color by using

Pack Test WAK-Cu manufactured by KYORITSU CHEMICAL-CHECK Lab., Corp., and this was quantified by using Digital Pack Test DPM-Cu manufactured by KYORITSU CHEMICAL-CHECK Lab., Corp. The point at which the copper ion concentration of the liquid B sampled was 0.15 mg/kg or more was taken as the permeation time of the copper ions.

The permeation time of the copper ions through the adhesion film B (thickness 20 μm) was determined by a similar operation. Additionally, the permeation time ratio of the permeation time of the adhesion film A with respect to the permeation time of the adhesion film B (the permeation time of the adhesion film A/the permeation time of the adhesion film B) was calculated. The results are shown in Table 4 below.

Figure 5:
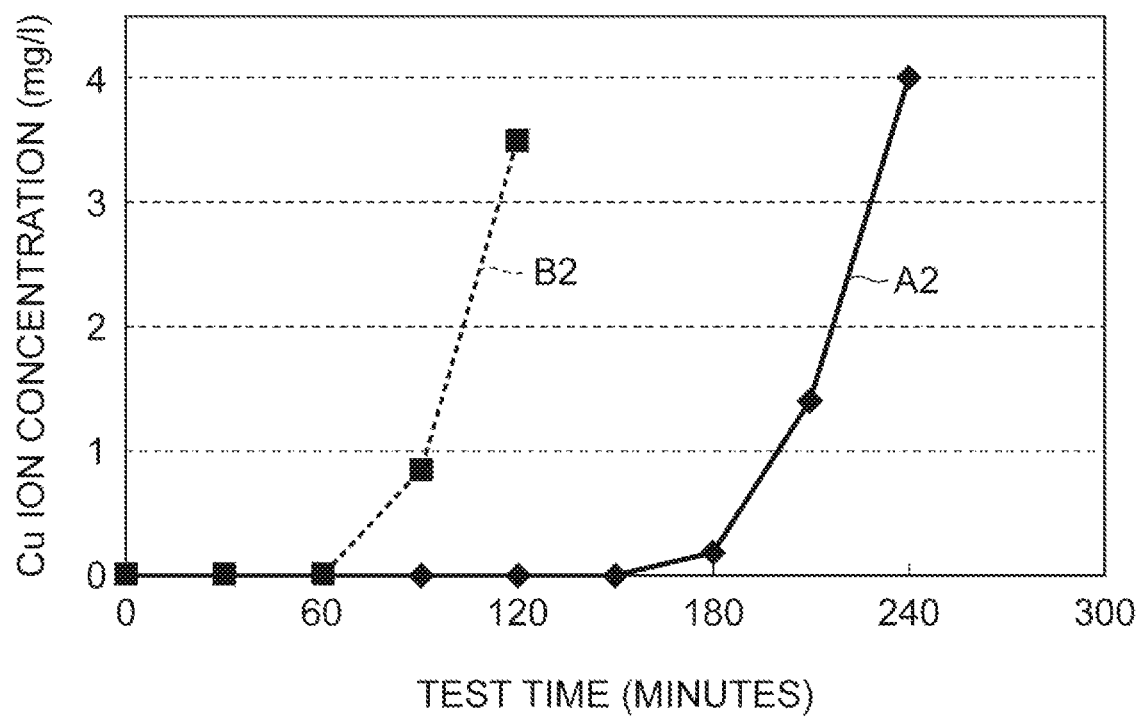
FIG. 5 is a view showing the measurement results of the copper ion concentration of Example 5.

Also, the measurement results of the copper ion concentration of Example 5 are shown in FIG. 5. In FIG. 5, the solid line A2 is the measurement result of the adhesion film A and the dotted line B2 is the measurement result of the adhesion film B.

Examples 5 to 10 and Comparative Example 4

The evaluation was made in the same manner as in Example 5 except that the components of the liquid B were replaced by the components shown in Tables 4 and 5 below. The results are shown in Tables 4 and 5.

TABLE 4

|  |  | Unit | Example 5 | Example 6 | Example 7 | Example 8 |
|---|---|---|---|---|---|---|
| Liquid A | Solvent | — | Water | Water | Water | Water |
|  | Heavy metal species | — | Copper | Copper | Copper | Copper |
|  | Heavy metal concentration | mg/kg | 500 | 0.5 | 5 | 5000 |
| Liquid B | Organic solvent species | — | NMP | NMP | NMP | NMP |
|  | Water/organic solvent proportion | Mass ratio | 50/50 | 50/50 | 50/50 | 50/50 |
|  | Additive species | — | Sodium sulfate | Sodium sulfate | Sodium sulfate | Sodium sulfate |
|  | Electrical conductivity | μS | 210 | 210 | 210 | 210 |
|  | Voltage applied | V | 24.0 | 24.0 | 24.0 | 24.0 |
| Results | Adhesion film A | Minutes | 180 | 420 | 180 | 180 |
|  | Adhesion film B | Minutes | 60 | 180 | 90 | 90 |

TABLE 4-continued

|  | Unit | Example 5 | Example 6 | Example 7 | Example 8 |
|---|---|---|---|---|---|
| Permeation time ratio of adhesion film A/B | — | 3.0 | 2.3 | 2.0 | 2.0 |
| Remark | — | — | — | — | — |

TABLE 5

| | | Unit | Example 9 | Example 10 | Comparative Example 4 |
|---|---|---|---|---|---|
| Liquid A | Solvent | — | Water | Water | Water |
| | Heavy metal species | — | Copper | Copper | Copper |
| | Heavy metal concentration | mg/kg | 50000 | 67500 | 0.1 |
| Liquid B | Organic solvent species | — | NMP | NMP | NMP |
| | Water/organic solvent proportion | Mass ratio | 50/50 | 50/50 | 50/50 |
| | Additive species | — | Sodium sulfate | Sodium sulfate | Sodium sulfate |
| | Electrical conductivity | μS | 210 | 210 | 210 |
| | Voltage applied | V | 24.0 | 24.0 | 24.0 |
| Results | Adhesion film A | Minutes | 180 | 120 | >2880 |
| | Adhesion film B | Minutes | 90 | 60 | >2880 |
| | Permeation time ratio of adhesion film A/B | — | 2.0 | 2.0 | — |
| | Remark | — | — | Salt precipitated in liquid A | No permeation could be detected |

As shown in the results of Examples, it is possible to easily and quickly evaluate the permeability of the heavy metal ions by using the permeability evaluation method of Examples, without requiring evaluation after the package was prepared. In Example 10, it was confirmed that it was possible to evaluate the permeability of the heavy metal ions although copper salt was precipitated in the liquid A. In contrast, in Comparative Example 4 where the copper ion concentration was low, it was not possible to quickly evaluate the permeability.

INDUSTRIAL APPLICABILITY

Because the permeability evaluation method of the present invention can easily and quickly evaluate the permeability of heavy metal ions through the insulating material used in semiconductor production (insulating material for semiconductors), the method can be exploited for evaluation of the gettering function of an insulating material for semiconductors, evaluation of the barrier ability, and material inspection method, for example. As a result, it is possible to make the method useful in development of highly reliable materials in ultra-thin PKG structures, quality control and the like.

REFERENCE SIGNS LIST

10, 10a, 10b: cell, 12, 12a, 12b: cell body, 14, 14a, 14b: opening portion, 16, 16a, 16b: flange portion, 20: direct-current power supply, 30: ammeter, 40: specimen, 40a, 40b: main surface, 50a, 50b: packing, 60a: positive electrode, 60b: negative electrode, 62a, 62b: clip, 70a, 70b, 70c, 70d: electric wiring, 100, 200: measuring apparatus, C: connecting portion, D: inner diameter.

The invention claimed is:

1. A permeability evaluation method for evaluating permeability of heavy metal ions through a specimen, comprising:
   a step of, in a state in which a first liquid containing heavy metal ions provided in a first cell and a second liquid containing water and an organic solvent provided in a second cell are separated by a specimen, applying a voltage between a positive electrode provided in contact with the first liquid and a negative electrode provided in contact with the second liquid and measuring a value of a current flowing between the positive electrode and the negative electrode,
   wherein the specimen contains an insulating material used in semiconductor production,
   a heavy metal ion concentration of the first liquid is 0.5 mg/kg or more, and
   evaluating the permeability of heavy metal ions based on the value of the current flowing between the positive electrode and the negative electrode.

2. The evaluation method according to claim 1, wherein the second liquid contains N-methyl-2-pyrrolidone as the organic solvent.

3. The evaluation method according to claim 2, wherein a content of N-methyl-2-pyrrolidone of the second liquid is 20% by mass or more and 80% by mass or less.

4. The evaluation method according to claim 1, wherein an electrical conductivity of the second liquid is 1 μS or more at 23° C.

5. The evaluation method according to claim 1, wherein the first liquid contains copper ions as the heavy metal ions.

6. The evaluation method according to claim 5, wherein a copper ion concentration of the first liquid is 0.5 to 50000 mg/kg.

7. The evaluation method according to claim 1, wherein the insulating material used in semiconductor production is adhesive tape for a semiconductor.

8. A permeability evaluation method for evaluating permeability of heavy metal ions through a specimen, comprising:
- a step of, in a state in which a first liquid containing heavy metal ions provided in a first cell and a second liquid containing water and an organic solvent provided in a second cell are separated by a specimen, and, after applying a voltage between a positive electrode provided in contact with the first liquid and a negative electrode provided in contact with the second liquid, measuring a heavy metal ion concentration of the second liquid,
- wherein the specimen contains an insulating material used in semiconductor production, and
- a heavy metal ion concentration of the first liquid is 0.5 mg/kg or more, and
- evaluating the permeability of heavy metal ions based on the value of the heavy metal ion concentration of the second liquid.

9. The evaluation method according to claim 8, wherein the second liquid contains N-methyl-2-pyrrolidone as the organic solvent.

10. The evaluation method according to claim 9, wherein a content of N-methyl-2-pyrrolidone of the second liquid is 20% by mass or more and 80% by mass or less.

11. The evaluation method according to claim 8, wherein an electrical conductivity of the second liquid is 1 μS or more at 23° C.

12. The evaluation method according to claim 8, wherein the first liquid contains copper ions as the heavy metal ions.

13. The evaluation method according to claim 12, wherein a copper ion concentration of the first liquid is 0.5 mg/kg to 50000 mg/kg.

14. The evaluation method according to claim 8, wherein the insulating material used in semiconductor production is adhesive tape for a semiconductor.

15. A permeability evaluation method for evaluating permeability of heavy metal ions through a specimen, comprising:
- a step of, in a state in which a first liquid containing heavy metal ions and a second liquid containing water and an organic solvent are provided in a cell and separated by a specimen, applying a voltage between a positive electrode provided in contact with the first liquid and a negative electrode provided in contact with the second liquid and measuring a value of a current flowing between the positive electrode and the negative electrode,
- wherein the specimen contains an insulating material used in semiconductor production,
- a heavy metal ion concentration of the first liquid is 0.5 mg/kg or more, and
- evaluating the permeability of heavy metal ions based on the value of the current flowing between the positive electrode and the negative electrode.

16. The evaluation method according to claim 15, wherein the second liquid contains N-methyl-2-pyrrolidone as the organic solvent.

17. The evaluation method according to claim 16, wherein a content of N-methyl-2-pyrrolidone of the second liquid is 20% by mass or more and 80% by mass or less.

18. The evaluation method according to claim 15, wherein an electrical conductivity of the second liquid is 1 μS or more at 23° C.

19. The evaluation method according to claim 15, wherein the first liquid contains copper ions as the heavy metal ions.

20. The evaluation method according to claim 19, wherein a copper ion concentration of the first liquid is 0.5 to 50000 mg/kg.

21. The evaluation method according to claim 15, wherein the insulating material used in semiconductor production is adhesive tape for a semiconductor.

22. A permeability evaluation method for evaluating permeability of heavy metal ions through a specimen, comprising:
- a step of, in a state in which a first liquid containing heavy metal ions and a second liquid containing water and an organic solvent are provided in a cell and separated by a specimen, and, after applying a voltage between a positive electrode provided in contact with the first liquid and a negative electrode provided in contact with the second liquid, measuring a heavy metal ion concentration of the second liquid,
- wherein the specimen contains an insulating material used in semiconductor production, and
- a heavy metal ion concentration of the first liquid is 0.5 mg/kg or more, and
- evaluating the permeability of heavy metal ions based on the value of the heavy metal ion concentration of the second liquid.

23. The evaluation method according to claim 22, wherein the second liquid contains N-methyl-2-pyrrolidone as the organic solvent.

24. The evaluation method according to claim 23, wherein a content of N-methyl-2-pyrrolidone of the second liquid is 20% by mass or more and 80% by mass or less.

25. The evaluation method according to claim 22, wherein an electrical conductivity of the second liquid is 1 μS or more at 23° C.

26. The evaluation method according to claim 22, wherein the first liquid contains copper ions as the heavy metal ions.

27. The evaluation method according to claim 26, wherein a copper ion concentration of the first liquid is 0.5 to 50000 mg/kg.

28. The evaluation method according to claim 22, wherein the insulating material used in semiconductor production is adhesive tape for a semiconductor.

* * * * *